United States Patent [19]

Manner

[11] 3,998,888
[45] Dec. 21, 1976

[54] SYNTHESIS OF SULFONYL PEROXIDES
[75] Inventor: James A. Manner, Akron, Ohio
[73] Assignee: PPG Industries, Inc., Pittsburgh, Pa.
[22] Filed: Nov. 12, 1975
[21] Appl. No.: 631,008
[52] U.S. Cl. .......................................... 260/607 R
[51] Int. Cl.² ..................................... C07C 147/00
[58] Field of Search .................. 260/607 R, 453 RZ
[56] References Cited
UNITED STATES PATENTS
3,586,722  6/1971  Sanchez et al. ............... 260/607 R
FOREIGN PATENTS OR APPLICATIONS
840,093  2/1941  Germany ...................... 260/607 R
OTHER PUBLICATIONS
Orthner; Angew. Chem. (1950) 62, pp. 382–385.
Graf; Ann. Chem. (1952) pp. 50–82, 578.

Primary Examiner—Lewis Gotts
Assistant Examiner—D. R. Phillips
Attorney, Agent, or Firm—William M. Dooley

[57] ABSTRACT

Sulfonyl peroxides represented by the formula

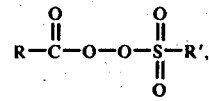

wherein R and R' independently are alkyl, cycloalkyl, or substituted alkyl or cycloalkyl groups having 1 to 20 carbons, are prepared in a liquid reaction phase by the sulfoxidation of an alkane or cycloalkane reactant with $SO_2$ and $O_2$ and acylation of the sulfoxidation product with a carboxylic acid anhydride. In the practice of this invention, an inert, immiscible organic solvent for the sulfonyl peroxide is introduced into the liquid reaction phase to dissolve the peroxide as it is formed and to produce a lower crude product phase containing the sulfonyl peroxide already dissolved in the inert solvent.

18 Claims, No Drawings

SYNTHESIS OF SULFONYL PEROXIDES

BACKGROUND OF THE INVENTION

1. Field of the Invention

This invention relates to the preparation of sulfonyl peroxides. More particularly, it relates to the preparation of sulfonyl peroxides such as acetyl cyclohexanesulfonyl peroxide by reaction of $SO_2$ and $O_2$ with an alkane or cycloalkane reactant and acylation with a carboxylic acid anhydride.

2. Description of the Prior Art

The basic process for the preparation of sulfonyl peroxides by sulfoxidation of saturated hydrocarbons and subsequent acylation with carboxylic acid anhydrides is shown in two references: L. Orthner, Angew. Chem., 62 302–5 (1950) and R. Graf, Ann. Chem., 578, 50–82 (1952). U.S. Pat. No. 3,586,722 to Sanchez (1971) describes the preparation of certain sulfonyl peroxides by the method of Graf and Orthner.

German Pat. No. 840,093 (1952) reports the preparation of alkanesulfonic acids by sulfoxidation of a saturated, non-aromatic hydrocarbon such as propane, n-butane, 3-methylheptane, cyclohexane, and methylcyclohexane and continuous extraction of product from the reaction mixture. Extraction may be performed in the sulfoxidation reactor or in an external extraction column. Suitable extraction solvents are immiscible with the hydrocarbon and include water, liquid sulfur dioxide, alcohols, low molecular weight fatty acids, acetonitrile, acetic anhydride, and mixtures of solvents as mixtures of methanol and water.

When sulfonyl peroxides are prepared by the method of Graf and Orthner, the product usually separates as a crude oily layer beneath the hydrocarbon reaction phase in the reactor. Both the crude oily products and the pure peroxides present a danger of violent decomposition or explosion and, although the crude oils are less dangerous than the pure peroxides, strong safety precautions such as heavy shielding, bunkers, and remote control of equipment should be employed in constructing a reactor.

The Sanchez patent shows the preparation of sulfonyl peroxides in a single liquid phase having a saturated hydrocarbon dissolved in a polar solvent which is inert to sulfoxidation, such as methylene chloride. The peroxide is obtained in solution in the polar solvent, and is then isolated by vacuum stripping.

Sulfonyl peroxides are much less dangerous when in solution, and solutions in certain solvents have commercial utility. For example, acetyl cyclohexanesulfonyl peroxide is a widely used polymerization initiator. When dry, it forms crystals which can detonate on minor impact. It is commonly sold dissolved in dimethyl phthalate, typically in concentrations of about 10 to about 35 weight percent, because the presence of small amounts of phthalate ester in finished polymers is often acceptable, whereas the presence of another solvent, methylene chloride for example, would not be acceptable.

The German patent recognizes that the sulfoxidation reaction may be carried out in the presence of an immiscible solvent. However, Graf, Orthner, and Sanchez all state that olefins and aromatic hydrocarbons, e.g., benzene, are inhibitors of the sulfoxidation reaction. Accordingly, no report has been found describing preparation of sulfonyl peroxides by sulfoxidation of saturated hydrocarbons and acylation with carboxylic acid anhydrides in the presence of aromatic solvents.

SUMMARY OF THE INVENTION

It has now been discovered that sulfonyl peroxides may be prepared in a liquid reaction phase by sulfoxidation of an alkane reactant with sulfur dioxide and oxygen and reaction of the sulfoxidation product with a carboxylic acid anhydride in the presence of an inert, immiscible organic solvent, such as a dialkyl ester if phthalic acid, introduced into the reaction phase as an immiscible solvent or extractant to form a lower crude product phase containing the sulfonyl peroxide already dissolved in the inert solvent. By forming the peroxide in the presence of inert, immiscible solvent in the reaction phase, rather than by diluting the crude product after it separates as an oily layer beneath the reaction phase, the possibility of dangerous concentrations of peroxide within the reactor is minimized, and the peroxide may be recovered directly (after washing and drying) in useable solution form. A mixture of inert, immiscible solvent and carboxylic acid anhydride may be introduced into the reaction phase. In a preferred embodiment, all reagents are introduced continuously into the reaction phase and product solution is recovered continuously from the product phase.

DETAILED DESCRIPTION OF THE INVENTION

In accordance with this invention, sulfonyl peroxides represented by the structural formula:

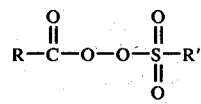

wherein R and R' independently are saturated alkyl, cycloalkyl, or substituted alkyl or cycloalkyl groups having 1 to 20 carbons, are prepared by introducing sulfur dioxide gas and an oxygen-containing gas into a liquid reaction phase containing an alkane reactant, R'H, and then simultaneously introducing into the reaction phase a carboxylic acid anhydride,

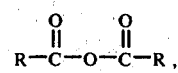

and an inert solvent for the sulfonyl peroxide which is immiscible with the reaction phase. A lower liquid product phase, which contains the sulfonyl peroxide dissolved in the inert solvent, forms beneath the reaction phase. A solution of the sulfonyl peroxide in the inert solvent may be recovered from the product phase. In a preferred embodiment, sulfur dioxide, oxygen, alkane reactant, carboxylic acid anhydride and inert, immiscible solvent are all introduced continuously into a liquid reaction phase, and a solution of sulfonyl peroxide in inert solvent is continuously withdrawn from a lower liquid product phase.

A suitable reactor for this invention will typically take the form of an unpacked, vertical column with reactant inlets at the top, a gas inlet at an intermediate point between the top and the bottom, usually below the mid-point, a product outlet at the bottom, and separate heating or cooling coils or jackets above and below the gas inlet. During operation, the column will be substantially filled with liquid in two phases, the interface between the phases being below the gas inlet.

The upper phase will be the reaction phase, and the lower phase will be the product phase.

Alkane reactants useful in the practice of this invention are alkanes and cycloalkanes having 1 to 20 carbons, preferably 4 to 12 carbons, including, for example, n-propane, isopropane, n-butane, 2-methylpropane, n-hexane, n-decane, 2-methylbutane, cyclohexane, methylcyclohexane, cyclopentane, cycloheptane, decalin, adamantane, n-hexadecane, 2-ethylheptane, n-nonane, n-hexadecane, and n-dodecane, and the corresponding halo, cyano, azido, carboxy, lower alkoxycarbonyl or lower acyloxy substituted alkanes and cycloalkanes. The higher alkanes are more subject to multiple sulfoxidation. Cycloalkanes having 5 or 6 ring carbons, such as cyclohexane, methylcyclohexane, and cyclopentane, are preferred. Cyclohexane is particularly preferred especially where a pure product substantially free of multiple sulfoxidation and of sulfoxidation isomers is desired. As used in the specification and the claims, the term "alkane reactant" is intended to mean the alkanes, cycloalkanes, and substituted alkanes and cycloalkanes described in this paragraph.

Useful carboxylic acid anhydrides,

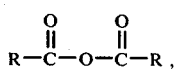

are those wherein each R independently is an alkyl or cycloalkyl group having from 1 to 20, preferably 1 to 6 carbons, or a corresponding halo, cyano, azido, carboxy, lower alkoxycarbonyl or lower acyloxy substituted alkyl or cycloalkyl group. Acetic anhydride is preferred because it is cheap, is not itself appreciably sulfoxidized, and has high reactivity in the formation of acetyl sulfonyl peroxides. Its low molecular weight does not unduly diminish the proportion of active oxygen in the peroxide product. In addition, the decomposition products of acetyl sulfonyl peroxides used as polymerization initiators are often more acceptable than those of other acyl sulfonyl peroxides. Mixed anhydrides, dicarboxylic acid dianhydrides, and cyclic anhydrides may also be employed. Useful carboxylic acid anhydrides include, for example, propanoic acid anhydride, 2-methylpropanoic acid anhydride, butanoic acid anhydride, acetic propanoic anhydride, decanoic acid anhydride, hexadecanoic acid anhydride, cyclohexanecarboxylic acid anhydride, succinic acid anhydride, glutaric acid anhydride, and malonic acid diacetic anhydride.

Both the alkane reactant and the carboxylic acid anhydride may bear inert substituents, i.e., substituents which do not inhibit the desired reactions or participate in them, in addition to those specifically mentioned.

The oxygen-containing gas is one containing elemental oxygen, $O_2$. The elemental oxygen may be diluted with an inert gas such as nitrogen, argon, or helium, but substantially pure oxygen, such as that obtained by fractional distillation of liquid air, is preferred. However, if diluted oxygen is used instead, the inert gas content causes violent bubbling in the reaction phase, and the through-put capacity of the reactor is reduced. The use of air instead of undiluted oxygen reduced the capacity of a reactor by about half.

The inert, immiscible solvent may be any organic solvent which is capable of forming a solution of acyl alkanesulfonyl peroxide of useful concentration, i.e., at least about 5 weight percent, which is inert, i.e., which does not inhibit the desired reactions, itself become sulfoxidized, or react with carboxylic acid anhydrides, and which is immiscible with the reaction phase. Dialkyl esters of phthalic acid, wherein the alkyl substituents are lower alkyl of from 1 to 12 carbons, preferably 1 to 4 carbons, are especially useful solvents. Useful phthalic acid diesters include, for example dimethyl phthalate, diethyl phthalate, dibutyl phthalate, methyl ethyl phthalate, methyl propyl phthalate, dioctyl phthalate, and mixtures thereof such as a mixture of dimethyl and diethyl phthalates. Other useful solvents include mono- and ortho-bromobenzenes and chlorobenzenes, alkyl esters of benzoic acid such as methyl benzoate, polychlorinated and polybrominated alkanes of 2 to 4 carbons such as 1,1,2,2-tetrachloroethane. The more heavily halogen-substituted alkanes will be more resistant to sulfoxidation; each carbon in the solvent should have at least one halogen and no more than 2 hydrogens. Although many immiscible liquids are partially soluble in one another, it is contemplated that the inert solvent will be introduced into the reaction phase in a proportion which is in fact immiscible under the operating conditions employed. With the use of phthalate esters in the practice of this invention, sulfonyl peroxides may be prepared, recovered, purified, and used in solution form. From the moment the peroxide is formed in the reaction phase, solvent is present to dilute and make it less hazardous, and because the solvent is acceptable in commercial applications, the peroxide need never be isolated in pure form.

In the practice of this invention, sulfur dioxide gas and oxygen-containing gas are introduced into a liquid reaction phase containing the alkane reactant. Therefore, temperatures and pressures consistent with those physical states are to be used. Temperatures of from about 0° C. to about 35° C. are useful. Higher temperatures may be dangerous; at lower temperatures the reaction may be too slow. Temperature of from about 25° C. to about 35° C. are preferred.

The hydrocarbon reactant is usually present in the reaction phase in excess at any given time. In continuous operation, alkane reactant is added to the reaction phase at a molar rate equal to the rate of anhydride addition plus an additional amount to compensate for unreacted alkane reactant carried into the product phase.

Sulfur dioxide and oxygen-containing gas are introduced into the reaction phase in a molar ratio of $SO_2:O_2$ of from about 1.75:1 to about 2.5:1 or higher. The gases may be mixed before being introduced. A ratio of from about 2.0:1 to about 2.3:1 is preferred. If too low a ratio is used, e.g., about 1.6:1, the sulfoxidation reaction may stop. Some of the sulfur dioxide dissolves in the inert, immiscible solvent without reacting, and is removed later in product workup. Gas flow rates are adjusted to minimize the amount of gas passing through the reaction phase without being absorbed. Introduction of the gases as well-dispersed, fine bubbles, for example from a glass frit, significantly aids absorption. Poor gas absorption lowers yield.

The inert solvent is used in an amount adequate to dissolve all of the sulfonyl peroxide present in the reactor. Preferably the rate of solvent addition is adjusted so that the solution of peroxide withdrawn from the subjacent product phase is of the desired concentration for use or sale.

For greatest efficiency, the molar rate of carboxylic acid anhydride addition is preferably about equal to the molar rate of oxygen addition. The molar ratio of anhydride to oxygen used may vary from about 1:1 to about 3:5, if desired. An excessive amount of anhydride may stop the reaction, while too small an amount will permit the formation of by-products and lead to reduced yield.

The manner in which the product solvent is introduced is of importance in the practice of this invention. The product solvent is chosen so that it disperses within the reaction phase as a separate solvent or extractant phase, and so that the solution of product in solvent forms a lower liquid product phase. The product phase should have a specific gravity sufficiently greater than that of the reaction phase to permit good phase separation. The solvent is introduced directly into the reaction phase above the interface between the reaction and product phases. For greatest safety, it is desirable to introduce the solvent as high as possible in the reaction phase, preferably at or near the surface. More preferably the solvent and the carboxylic acid anhydride are introduced at the surface of the reaction phase together in admixture. This provides an additional margin of safety: when solvent is introduced separately, an interruption in its flow may allow concentrated sulfonyl peroxide to accumulate in the reactor, particularly at the interface between the reaction product phases. An interruption in the flow of the solvent anhydride mixture would simply stop the reaction. If desired, the solvent may be introduced below the point of introduction of the gases but above the interface between the reaction and product phases. When introduced there, the solvent will still serve to prevent accumulation of sulfonyl peroxide at the interface, but will pick up less sulfur dioxide and alkane reactant so that reactant losses and sulfur dioxide effluent from the product workup will be lessened.

Once it begins, the sulfoxidation reaction is self-sustaining, and may be stopped and started at will by controlling the flow of reactants. The reaction may be initiated by heating to about 50° C. or by exposure to ultraviolet radiation, e.g., a sunlamp. More conveniently, an organic peroxide such as diisopropyl peroxydicarbonate may be added initially to the reactant phase. Byproducts of the peroxide initiation are usually water soluble and can be removed during the washing and drying of the product solution.

Olefins and aromatic hydrocarbons other than those mentioned as inert solvents are known inhibitors of the sulfoxidation reaction and should be present in no more than trace amounts, if at all. Water and alcohols should not be present, because they react with carboxylic acid anhydride and also with the peroxysulfonic acid in the presence of sulfur dioxide to give unwanted sulfonic and sulfuric acids.

EXAMPLE I

A 300 milliliter, four-necked, baffled flask was equipped with a blade stirrer, a temperature regulator, an addition funnel, a bottom stopcock, a gas inlet tube, and a gas outlet tube.

Three milliliters of 40 percent peracetic acid was added with vigorous stirring to 200 of cyclohexane in the flask. A mixture of sulfur dioxide (0.16 moles/hour) and oxygen (0.08 moles/hour) was then bubbled through the cyclohexane, which became cloudy after 10 minutes. Then a mixture of 16.4 grams (0.16 mole) of acetic anhydride and 64 grams of dimethyl phthalate was added dropwise over a period of 2 hours at 28°–30° C. Temperature was maintained by spraying the flask with warm water. After 2 hours, the bottom oil layer which had formed was drawn off and discarded. Then an additional 16.4 grams of acetic anhydride in 64 grams of dimethyl phthalate was added dropwise with vigorous stirring. During the third hour, exit gas flow dropped off and the reaction temperature was maintained at 30°–30.5° C. with occasional cooling. At the end of the fourth hour, the bottom oil layer was again withdrawn. The cycle was repeated and another oil sample taken at the end of the sixth hour.

The oil samples were cooled in ice water for about 10 minutes and the upper, cyclohexane layer was removed. They were then washed, phase separated, and vacuum stripped at 5–10 millimeters of mercury for 25–30 minutes. A clear colorless liquid was obtained. The fourth hour sample of acetyl cyclohexanesulfonyl peroxide in dimethyl phthalate weighed 77.6 grams and contained a 38.2 percent yield of acetyl cyclohexanesulfonyl peroxide based on acetic anhydride added. The sixth hour sample weighed 93.0 grams and contained a 65 percent yield of acetyl cyclohexanesulfonyl peroxide.

EXAMPLE II

A reactor column 3.5 centimeters in outer diameter by 64 centimeters in length was equipped at the top with inlets for hydrocarbon, solvent/anhydride solution, and nitrogen purge gas, and a gas outlet. One fourth of the way from the bottom were a thermometer and a gas inlet: an extra coarse glass frit for dispersing pre-mixed sulfur dioxide and oxygen. A heating coil of 7 millimeter glass tubing was located above the frit and a cooling coil was located below. A bottom outlet was connected to a leveling arm for regulating the height of liquid in the reactor. Removable safety shields of ⅛ inch plastic were placed around the reactor. A three-way stopcock at the bottom outlet was arranged to permit emergency dumping of the reactor contents. The following procedure, with only slight variation, was used for all the experiments. About 130 milliliters of dimethyl phthalate was pumped into the reactor under nitrogen purge across the top and through the glass frit. Coolant at 6.5°–13° C. was circulated through the lower coil. Then 260–270 milliliters of cyclohexane containing 1.3 grams of diisopropyl peroxydicarbonate was pumped in, and water at 30° C. was circulated through the upper coil. After 30–60 minutes, nitrogen purge through the glass frit was discontinued and sulfur dioxide was bubbled through the cyclohexane phase until it was saturated. With the sulfur dioxide flow at 0.32 mole/hour, oxygen flow was started. After 15 minutes the cyclohexane solution had become cloudy.

After an additional 30 minutes of oxygen flow during which time the flow was gradually increased, one-fourth inch of yellow oil had accumulated between the cyclohexane and the dimethyl phthalate phases. Then addition of acetic anhydride in dimethyl phthalate (20.4 weight percent, 0.16 mole/hour) was started. Over the next 60 minutes, the oxygen flow rate was gradually increased to 66.6 cubic centimeters/minute, 0.16 mole/hour. Cyclohexane was initially pumped in at its stoichiometric rate of consumption, 0.16 mole/hour. The rate of cyclohexane addition was later increased slightly to maintain the liquid level and to compensate for losses to the product-dimethyl phthalate phase. Vigorous bubbling was observed at the surface of the cyclohexane phase during the first 2 hours of operation, but gradually subsided.

Product continuously overflowing through the leveling arm was collected in ice cooled receivers. Hourly samles were washed twice with equal volumes of cool water and were vacuum stripped at 5–10 millimeters of mercury for about 25 minutes.

Yields of acetyl cyclohexane sulfonyl peroxide and the concentrations of the product solution varied considerably during the first 4 to 5 hours of operation. In one run of 4 to 5 hours duration, the overall yield was 63.5 weight percent and the product solution had an average assay of 25.4weight percent acetyl cyclohexanesulfonyl peroxide. In another, the overall yield for the final 3 hours of operation was 69.7 weight percent, and the overall assay was 28.43 weight percent. Table I shows the progress of a nine hour run.

TABLE I

| Hourly Sample | Moles Acetic Anhydride/hour | ACSP-DMP grams/hour[1] | Assay, % | ACSP grams/hour | Yield, %[2] |
|---|---|---|---|---|---|
| 1 | 0.11 | 68.2 | 0.66 | 0.45 | 1.8 |
| 2 | 0.15 | 102.9 | 9.50 | 9.8 | 29.4 |
| 3 | 0.14 | 89.1 | 28.76 | 25.6 | 82.3 |
| 4 | 0.18 | 104.8 | 28.96 | 30.4 | 76.0 |
| 5 | 0.13 | 86.0 | 27.81 | 23.9 | 82.7 |
| 6 | 0.17 | 97.8 | 29.47 | 28.8 | 76.2 |
| 7 | 0.17 | 98.9 | 28.62 | 28.3 | 74.9 |
| 8 | 0.16 | 103.7 | 28.70 | 29.8 | 83.9 |
| 9[3] | — | 79.2 | 29.06 | 23.0 | — |
| overall | 1.21 | 830.6 | 28.77[4] | 200.0 | 74.3 79.3[5] |

[1]Water washed, then degassed and dried on a rotary film evaporator
[2]Based on moles of acetic anhydride
[3]Composite sample: crude ACSP-DMP in bottom of reactor and leveling arm after shut down
[4]Average of samples 3 through 9
[5]Average of samples 3 through 8

In the experiment reported in Table I, the initiator was diisopropyl peroxydicarbonate and the mole ratio of sulfur dioxide to oxygen was 2.0 ACSP is acetyl cyclohexanesulfonyl peroxide and DMP is dimethyl phthalate. Assay is given in weight percent of ACSP in the ACSP-DMP solution.

Although this invention has been described with reference to particular details, the particulars are not intended to limit the invention except insofar as they appear in the following claims.

I claim:

1. In the process for producing an acyl alkanesulfonyl peroxide from an alkane reactant and a carboxylic acid anhydride by the introduction of sulfur dioxide gas, an oxygen-containing gas, and a carboxylic acid anhydride into a liquid reaction phase containing the alkane reactant, the improvement which comprises:
   introducing into the liquid reaction phase simultaneously with the introduction of the sulfur dioxide gas, the oxygen-containing gas, and the carboxylic acid anhydride, an inert solvent for the sulfonyl peroxide which is immiscible with the liquid reaction phase, and which forms lower liquid product phase containing sulfonyl peroxide dissolved in inert solvent, the solvent being a dialkyl ester of phthalic acid, wherein the alkyl groups have from 1 to 12 carbons, and
   recovering from the product phase a solution of acyl alkanesulfonyl peroxide in dialkyl ester of phthalic acid.

2. The process of claim 1 conducted at a temperature between about 0° C. and about 35° C.

3. The process of claim 2 wherein the carboxylic acid anhydride is acetic anhydride, the alkane reactant is a cycloalkane having 5 to 6 ring carbons, and the inert solvent is a dialkyl ester of phthalic acid wherein the alkyl groups have from 1 to 4 carbons.

4. The process of claim 3 wherein the cycloalkane is cyclohexane and the inert solvent is dimethyl phthalate.

5. The process of claim 3 wherein the cycloalkane is cyclohexane and the inert solvent is a mixture of dimethyl phthalate and diethyl phthalate.

6. The process of claim 1 wherein a mixture of the carboxylic acid anhydride and the inert solvent is introduced into the liquid reactant phase.

7. The process of claim 6 wherein the mixture is introduced at the upper surface of the liquid reactant phase.

8. The process of claim 1 wherein the inert solvent is introduced into the liquid reactant phase above the product phase but below the point where the sulfur dioxide is introduced.

9. The process of claim 1, wherein the inert solvent is a mixture of dialkyl esters of phthalic acid.

10. A continuous process for the production of acetyl cyclohexanesulfonyl peroxide from cyclohexane and acetic anhydride which comprises:
   continuously introducing into a liquid cyclohexane-containing reaction phase cyclohexane, sulfur dioxide gas, oxygen-containing gas, acetic anhydride, and dialkyl ester of phthalic acid having alkyl groups of from 1 to 12 carbons to form a lower liquid product phase containing acetyl cyclohexanesulfonyl peroxide dissolved in dialkyl ester of phthalic acid, and
   continuously recovering from the product phase a solution of acetyl cyclohexanesulfonyl peroxide in dialkyl ester of phthalic acid.

11. The process of claim 10 conducted at a temperature of from about 0° C. to about 35° C.

12. The process of claim 10 wherein the dialkyl ester of phthalic acid is dimethyl phthalate.

13. The process of claim 10 wherein the dialkyl ester of phthalic acid is a mixture of dimethyl phthalate and diethyl phthalate.

14. The process of claim 10 wherein the solution of acetyl cyclohexanesulfonyl peroxide in dialkyl ester of phthalic acid has a concentration of from about 10 to about 35 weight percent.

15. The process of claim 10 wherein a mixture of acetic anhydride and dialkyl ester of phthalic acid is introduced into the liquid reactant phase.

16. The process of claim 15 wherein the dialkyl ester of phthalic acid is dimethyl phthalate.

17. The process of claim 10 wherein the dialkyl ester of phthalic acid is introduced into the liquid reactant phase above the product phase but below the point where the sulfur dioxide is introduced.

18. The process of claim 10, wherein the dialkyl ester of phthalic acid is a mixture of dialkyl esters of phthalic acid.

* * * * *